United States Patent [19]

Lloyd

[11] Patent Number: 5,568,747
[45] Date of Patent: Oct. 29, 1996

[54] MOISTURE SENSOR

[76] Inventor: Robert H. Lloyd, 13, Ranmore Road, Dorking, Surrey RH4 1H3, Great Britain

[21] Appl. No.: 256,342
[22] PCT Filed: Jan. 8, 1993
[86] PCT No.: PCT/GB93/00024
  § 371 Date: Sep. 12, 1994
  § 102(e) Date: Sep. 12, 1994
[87] PCT Pub. No.: WO93/14395
  PCT Pub. Date: Jul. 22, 1993

[30] Foreign Application Priority Data

Jan. 13, 1992 [GB] United Kingdom .................. 9200583

[51] Int. Cl.⁶ ........................... G01N 25/56; G01R 27/08
[52] U.S. Cl. ................ 73/73; 324/694; 324/724
[58] Field of Search .................... 73/73, 335.05; 324/694, 696, 724; 338/13, 195, 229

[56] References Cited

U.S. PATENT DOCUMENTS 2,740,032  3/1956  Bouyoucos ...................... 324/696 X
3,824,844  7/1974  Strickland ...................... 73/73
4,449,396  5/1984  Bzdula .......................... 324/696 X

FOREIGN PATENT DOCUMENTS 091547   1/1986  European Pat. Off. .
3538463  10/1985  Germany .
63-47902  2/1988  Japan ........................... 324/694
2091880   8/1982  United Kingdom ............ 324/694

Primary Examiner—William A. Cuchlinski, Jr.
Assistant Examiner—Willie Morris Worth

[57] ABSTRACT

The moisture sensor comprises a block of absorbent material, such as wood. Two opposed faces are coated with conductive material, such as paint and two conductors of a cable are connected to the conductive material. The entire element is encapsulated within a sleeve of electrically insulating material, leaving one end face of the block of moisture absorbent material exposed. A plurality of apertures or perforations are provided in the sleeve exposing at least part of the moisture absorbent material. The sensor is adapted to be exposed to an environment to sense the moisture level of that environment.

12 Claims, 1 Drawing Sheet

MOISTURE SENSOR

BACKGROUND OF THE INVENTION

The present invention relates to a moisture sensor and more particularly to a moisture sensor adapted to be used to sense the moisture content within wood, although the sensor of the invention may find other applications.

It is to be appreciated that the performance and durability of wood is dependent upon its moisture content. It is thus desirable to be able to measure the moisture content of wood.

Many moisture meters have been proposed previously which can measure the moisture content of wood, but most of these meters rely on inserting two prongs or electrodes into the wood, and then measuring the electrical resistance between the prongs or electrodes.

Such a technique is very prone to error, since the electrical resistance between the prongs depends upon the degree of insertion into the wood, the nature of any paint provided on the exterior of the wood, and many other similar factors. Also such moisture meters can only be used to determine the moisture of wood where access can be gained to the surface of the wood.

The present invention seeks to provide an improved moisture sensor.

SUMMARY OF THE INVENTION

According to this invention there is provided a moisture, sensor, the sensor comprising an elongate element of moisture absorbent material presenting two opposed side faces, the two opposed side faces being provided with conductive material extending over a predetermined area thereof, there being a cable having two conductors which are connected respectively to the areas of electrically conductive material, the element being encapsulated within a sleeve of electrically insulating material, the sleeve being such that an end face of the sensor is exposed, there being a plurality of apertures or perforations in the sleeve exposing at least part of the element, the sensor being adapted to be exposed to an environment, the moisture level of which is to be sensed by the sensor.

Preferably the apertures of perforations are provided at the ends of bores extending through the element.

conveniently the bores extend through parts of the element which are not provided with said conductive material.

Preferably the electrically conductive material is in the form of conductive paint, such as a silver paint.

Advantageously the conductors of the cable are secured or bonded to the conductive material.

Advantageously the absorbent material is wood.

Conveniently the absorbent material has a size which is approximately 1.8 mm by 1.8 mm by 8 mm.

The sleeve may be a heat-shrunk sleeve of plastic material which covers the conductive material.

The invention also relates to the use of a sensor as described above with a moisture meter or a moisture monitor, and the sensor may be interrogated by a microprocessor. The sensor may be interrogated over a telephone line or the like by a remote computer.

BRIEF DESCRIPTION OF THE DRAWING

In order that the invention may be more readily understood, and so that further features thereof may be appreciated, the invention will now be described, by way of example, with reference to the accompanying drawings in which.

DETAILED DESCRIPTION OF THE INVENTION

A moisture sensor in accordance with the invention has a sensor strip 1 which is formed from an appropriate element of a moisture absorbent material, such as wood. The wood may be any appropriate wood, but is preferably a uniform close-grained wood, so that sensor strips for sensors in accordance with the invention may be substantially uniform. The strip 1 is an elongate strip of square cross-section. The strips may be cut to have approximately the desired size and the strips may then be brought to an accurate size by dry sanding or abrading. This will also remove splinters. It has been found that the sensor strip 1 may suitably have a final size of 1.8 mm by 1.8 mm by 8 mm. Of course, this is one example of a size that may be used for embodiments of the invention, but other sizes may prove to be adequate, be they larger or smaller.

It is to be understood that the moisture content of the wood strip must be monitored and controlled, so that accurate dimensions for the finished sensor may be obtained. Preferably the strip should have a uniform moisture content of between 6 and 9 percent.

Figure 1:
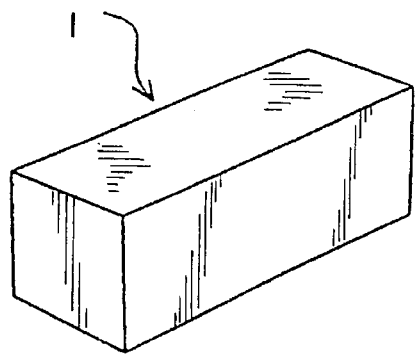
FIG. 1 is a perspective view of a sensor strip to be used in a sensor in accordance with the invention.
Figure 2:
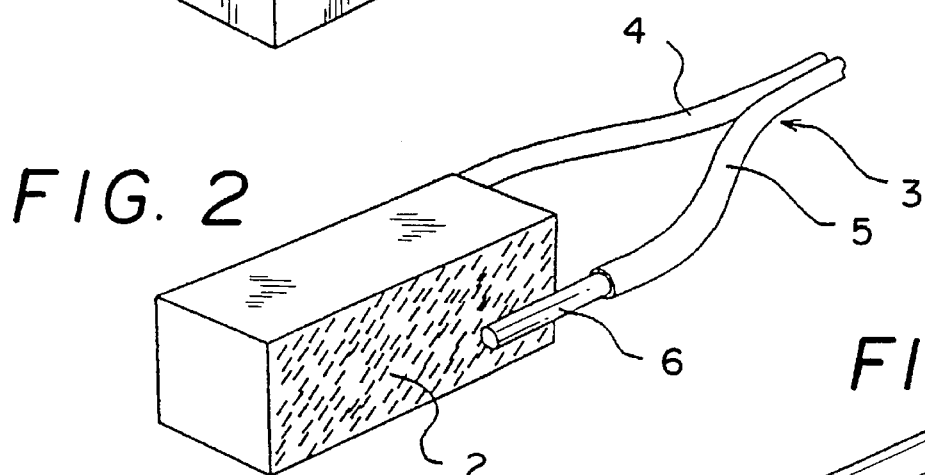
FIG. 2 shows a perspective view of the sensor strip of FIG. 1 with wires attached.
Figure 3:
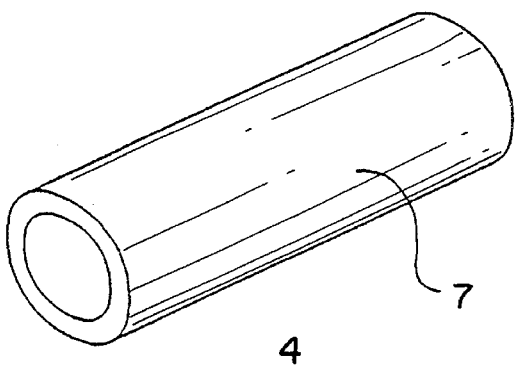
FIG. 3 shows a perspective view of a heat shrinkable sleeve.
Figure 5:
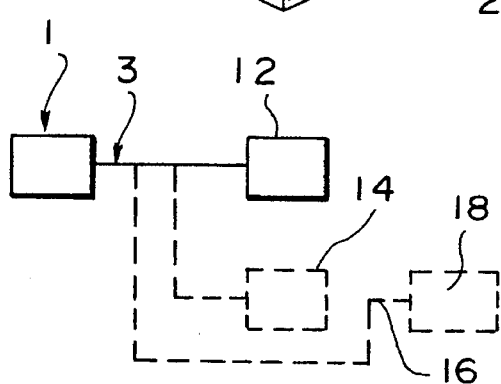
FIG. 5 shows a schematic diagram of system wherein the sensor of the present invention is connected to a meter, monitor or a remote central computer.

When the sensor strip 1 has been fabricated to the desired size, two opposed elongate faces 2 which may be termed "radial" faces, are painted with electrically conductive silver paint. Any appropriate silver paint may be used, Such as ALTA 1 electrically conductive paint (Catalogue number 1 SECP). Only one of the faces 2 coated with silver paint is visible in FIG. 2. Care is taken to remove silver paint from all the other faces, or preferably to ensure that none of the paint is applied to the other faces. A cable 3 having two conductive wires 4, 5, is taken and the end portions 6 of the wires are bared, and the bared wires are then placed in contact with the respective silver painted faces 2 of the sensor strip 1, and clamped in position. The bared wires become bonded or adhered to the silver paint as it dries. For example approximately 6.5 mm of bare wire may be bonded to each silver painted face 2 of the sensor strip 1.

Next, the sensor is encapsulated in a strong electrically insulating water impermeable material. Thus, for example, a sleeve 7 of heat shrinkable plastics material is mounted on the assembly thus fabricated, to cover the entire length of the sensor strip 1, and to cover part of the cable 3. The sleeve 7 is then heat-shrunk into position, to form an encapsulation 8. The sensor strip 1 is thus substantially encapsulated, whilst leaving an end face 9 of the sensor strip exposed. The rest of the sensor is substantially sealed.

Figure 4:
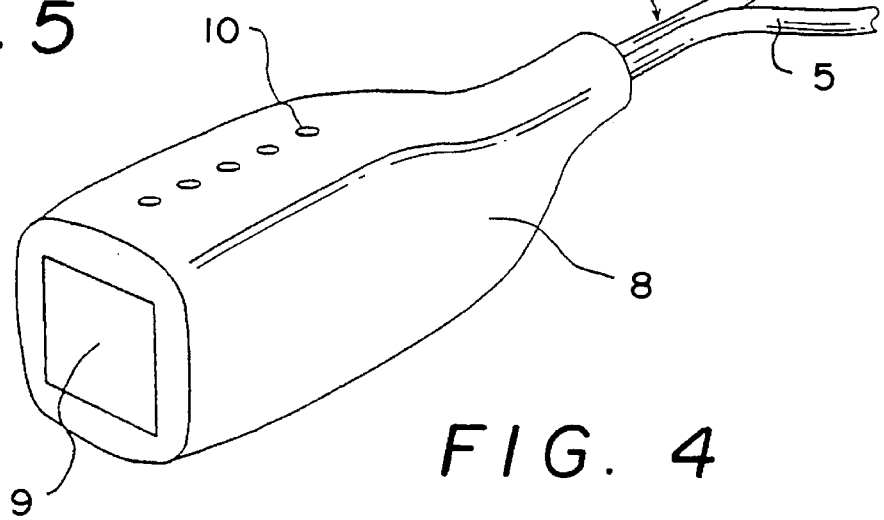
FIG. 4 shows a perspective view of the assembled sensor.

A plurality of apertures are formed in the encapsulation, aligned with the elongate faces of the sensor strip 1 which are not provided with the silver paint. In the embodiment illustrated in FIG. 4, five apertures 10 are provided. The apertures are evenly spaced and each have a diameter of approximately 0.5 mm. The apertures, in this embodiment, do not simply expose the unpainted side faces of the sensor strip, but instead form the ends of bores which extend through the sensor strip and out of the other side of the encapsulation. Thus, various regions of, the sensor strip are exposed including the end face 9 and the interior of each of the bores defined by the small holes or apertures 10.

The sensor may be trimmed to the desired length by cutting back the exposed face 9.

The fabricated sensor element is then permitted to reach an equilibrium moisture condition. This may be achieved by leaving the sensor within a standard environment for a specific period of time. The sensor element may then be connected to a resistance meter or moisture meter to check that the sensor element reads within a predetermined tolerance band.

It is to be appreciated that the electrical resistance of the sensor follows the equation:

$$R = r\frac{d}{A}$$

where
R= electrical resistance ohms
r= electrical resistivity, ohm/mm
d= is the distance between the electrodes in mm
A= is the area of each electrode in square mm.

It is possible to calibrate the sensor with regard to moisture content, the resistivity of the wood of the sensor varying with the moisture content of the wood.

A sensor element in accordance with the invention may be located permanently or semi-permanently in position in a piece of wood, the moisture content of which is to be monitored, with the cable 3 being accessible to a moisture meter 12. The sensor element 1 may thus be located in a position which ordinary would not be accessible. Thus the sensor of the present invention may be utilised with a moisture meter which can be releasably and reliably connected to the cable 3 with greater facility than the conventional moisture meter which involves the insertion of pins into the wood work. It is to be appreciated that the sensor of the invention may be located in position when a wooden structure is fabricated, and the cable 5 may come to a termination at a suitable place, thus meaning that decorations need not be damaged when the moisture level of wood is to be determined.

Alternatively, the sensor may be connected to a device with which it forms a moisture monitor 14, such as a micro-processor, which can effectively take readings of moisture level by interrogating the sensor from time-to-time. The measured readings may be recorded, and an alarm may be activated, or some device operated (such as a ventilating fan) if the measured value exceeds a predetermined limit, or is outside an acceptable range.

Such a micro-processor can be pre-programmed appropriately in accordance with the particular conditions under which the sensor is to be used.

The sensor may be interrogated from a remote location, for example over telephone lines 16, by a central computer 18.

It is to be appreciated that the heat-shrunk sleeve provides the sensor with protection against physical damage or contamination when it is inserted into position. It has been found that the encapsulation controls the response time of the sensor. Encapsulation of the sensor with the heat-shrunk sleeve makes possible a miniature sensor of robust construction capable of withstanding physical and thermal abuse without loss of performance.

The provision of the heat-shrunk sleeve also serves to isolate or insulate the sensor element electrically from the material in which it is installed, thus ensuring that the resistivity readings that are taken are taken solely across the sensor element. This allows the sensor element to be used in any type of material without any need for recalibration.

It is to be appreciated that the material forming the strip of the sensor is preferably wood, as described, but this need not be so, since any appropriate absorbent material with the requisite properties can be utilised.

The surface area of the sensor strip 1 that is exposed to the environment that is to be messed can be controlled by the encapsulation established by the heat-shrunk sleeve 8. Whilst in the described embodiment the entire end face 9 of the strip is exposed, a lesser area may be exposed if desired.

In alternative embodiments of the invention the bare wires may be adhered to the silver painted faces 2, when they have dried, using a cellulose acetate glue or other appropriate adhesive.

It is to be appreciated that the sensor is very small, and thus the sensor may be located in very small places. Also the sensor, since it is encapsulated, may be handled easily.

The provision of the apertures in the encapsulation and the associated bores permits the response time of the sensor to be initially selected. The bores serve the dual function of decreasing the mass of the sensor element, while increasing the surface area. Thus the greater the number of bores the faster is the response time. However, the provision of the apertures and the bores does not detract from the advantages of encapsulating the element.

Whilst the invention has been described with reference to the use of the sensor primarily to sense the moisture level present in timber, the sensor may be used to sense the moisture level present in the atmosphere, in a confined space, or in materials other than timber.

The features disclosed in the foregoing description, in the following claims and/or in the accompanying drawings may, both separately and in any combination thereof, be material for realising the invention in diverse forms thereof.

I claim:

1. A moisture sensor for sensing the moisture level of an environment, comprising:
    a) an element of moisture absorbent material having two opposed side faces, said opposed side faces being provided with electrically conductive material, said element having a resistivity that varies with the moisture content therein to provide an indication of the moisture level of the environment;
    b) a cable having two conductors disposed respectively on said opposed side faces and connected to said electrically conductive material; and
    c) an electrically insulating sleeve encapsulating said element such that an end face of said element is exposed, said sleeve including a plurality of apertures exposing at least part of said element.

2. A sensor as in claim 1, wherein:
    a) said element includes bores therein aligned with said apertures.

3. A sensor as in claim 2, wherein:
    a) said bores extend through said element between said opposed side faces.

4. A sensor as in claim 1, wherein:
    a) said electrically conductive material comprises a conductive paint.

5. A sensor as in claim 1, wherein:
a) said electrically conductive material is silver paint.

6. A sensor as in claim 1, wherein:
a) said conductors are bonded to said electrically conductive material.

7. A sensor as in claim 1, wherein;
a) said element is wood.

8. A sensor as in claim 1, wherein:
a) said element has a size approximately 1.8 mm high by 1.8 mm wide by 8 mm long.

9. A sensor as in claim 1, wherein:
a) said sleeve is made of heat-shrink plastic.

10. A sensor system for sensing the moisture level of an environment, comprising:
a) an element of moisture absorbent material having two opposed side faces, said opposed side faces being provided with electrically conductive material, said element having a resistivity that varies with the moisture content therein to provide an indication of the moisture level of the environment;
b) a cable having two conductors disposed respectively on said opposed faces and connected to said electrically conductive material;
c) an electrically insulating sleeve encapsulating said element such that an end face of said element is exposed, said sleeve including a plurality of apertures exposing at least part of said element; and
d) a moisture meter connected to said cable.

11. A sensor system for sensing the moisture level of an environment, comprising:
a) an element of moisture absorbent material having two opposed side faces, said opposed side faces being provided with electrically conductive material, said element having a resistivity that varies with the moisture content therein to provide an indication of the moisture level of the environment;
b) a cable having two conductors disposed respectively on said opposed faces and connected to said electrically conductive material;
c) an electrically insulating sleeve encapsulating said element such that an end face of said element is exposed, said sleeve including a plurality of apertures exposing at least part of said element; and
d) a monitor connected to said cable.

12. A sensor system, as in claim 11, wherein:
a) said monitor includes a micro-processor.

* * * * *